(12) United States Patent
Ismail

(10) Patent No.: US 8,404,285 B2
(45) Date of Patent: Mar. 26, 2013

(54) GUAVA PULP COMPOSITION

(75) Inventor: Amin Ismail, Selangor (MY)

(73) Assignee: Universiti Putra Malaysia, Selangor (MY)

( * ) Notice: Subject to any disclaimer, the term of this patent is extended or adjusted under 35 U.S.C. 154(b) by 72 days.

(21) Appl. No.: 13/058,479

(22) PCT Filed: Oct. 30, 2009

(86) PCT No.: PCT/MY2009/000179
§ 371 (c)(1),
(2), (4) Date: Mar. 17, 2011

(87) PCT Pub. No.: WO2010/053346
PCT Pub. Date: May 14, 2010

(65) Prior Publication Data
US 2011/0171327 A1    Jul. 14, 2011

(30) Foreign Application Priority Data

Nov. 10, 2008  (MY) ............................... PI 20084485

(51) Int. Cl.
*A01N 65/00*    (2009.01)
(52) U.S. Cl. ........................................................ 424/725
(58) Field of Classification Search ........................ None
See application file for complete search history.

(56) References Cited

U.S. PATENT DOCUMENTS

2005/0175672 A1*   8/2005   Kluetz et al. .................. 424/439

* cited by examiner

*Primary Examiner* — Michael Meller
(74) *Attorney, Agent, or Firm* — Lowe Hauptman Ham & Berner, LLP

(57) ABSTRACT

The present invention discloses a guava pulp (also referred to as pulp composition) of a particle size not greater than 0.25 mm which does not contain seeds and peels from the guava and has a lycopene concentration which is 1 to 2 folds higher than the lycopene concentration in the guavas from which the pulp is obtained. The invention further discloses uses of the pulp composition as starting material for obtaining guava oleoresin and lycopene, and as antioxidant.

1 Claim, 2 Drawing Sheets

GUAVA PULP COMPOSITION

RELATED APPLICATIONS

The present application is a national phase of PCT/MY2009/000179, filed Oct. 30, 2009 and is based on, and claims priority from, Malaysian Application Number PI 20084485, filed Nov. 10, 2008.

The present invention relates to the field of guava processing and products thereof. More particularly the present invention relates to a guava pulp composition having high lycopene concentration.

BACKGROUND TO THE INVENTION

Food industries generate large amount of wastes and by-products that contain highly valuable bioactive compounds The primary waste fraction, which are peel, flesh and seeds residues, contain high amount of bioactive compounds that can be exploited as functional foods, additives, nutraceutical products, health supplements, food ingredients and cosmetics.

Guava industry has produced an important quantity of by-products residues of which accounted 25% of the whole fruit. They are produced at different processing stages, which are crushing, refining and sieving to produce three types of by-products, namely refiner, siever and decanter respectively. Previous study showed that lycopene from guava pulp was higher than sweetened puree (Wilberd and Rodrigues-Amaya, 1995). Insufficient removal of solid particles especially the pulp consisting stone cells lead to the remaining of lycopene in processing by-products.

Lycopene is a carotenoid in the same family as beta carotene, which gives a tomato, and several other fruits, their deep red color. Lycopene is one of the major carotenoids in the diet of North Americans and accounts for close to 50% of the carotenoid distribution found in blood. Foods that are commonly consumed which contain lycopene are tomato products, watermelon, pink grapefruit, apricots, papaya, and guava.

So far, no prior art has disclosed a guava pulp composition having high lycopene content.

PCT/IL2003/000678 discloses a tomato pulp composition wherein the particle size is not greater than 2.5 mm which does not contain seeds or peels from the tomato and has a lycopene concentration which is 5 to 15 folds higher than the lycopene concentration in the tomatoes from which the pulp is obtained. This disclosure further describes an industrial process for obtaining the tomato pulp.

Accordingly, it is advantageous to provide a guava pulp composition having improved organoleptic properties. The guava pulp composition according to the present invention is produced under certain conditions in order to obtain a composition having high lycopene content.

SUMMARY OF THE INVENTION

An aspect of the present invention provides a guava pulp (also referred to as pulp composition) of a particle size not greater than 0.25 mm which does not contain seeds and peels from the guava and has a lycopene concentration which is 1 to 2 folds higher than the lycopene concentration in the guavas from which the pulp is obtained.

The pulp is subjected to heat treatment at 50° C. to 65° C. in order to increase the lycopene concentration in the guavas from which the pulp is obtained.

The pulp is further dried at 40° C. to 60° C. in order to remove about 50% water contained in the guavas from which the pulp is obtained.

Another aspect of the present invention provides the use of the pulp composition as starting material for obtaining guava oleoresin and lycopene.

According to a further aspect of the present invention, the composition of the present invention which has a high concentration of lycopene, may be used as an antioxidant, particularly as an antioxidant for food and edible products.

BRIEF DESCRIPTION OF THE DRAWINGS

FIGS. 1(a) and 1(b) show representative a guava pulp composition according to the present invention, i.e. LC-APCI-MS analysis of pink guava by-products extract, in which FIG. 1(a) is the cis-lycopene isomer m/z and FIG. 1(b) is the all-trans-lycopene isomer m/z.

DETAILED DESCRIPTION OF THE INVENTION

Figure 1A:
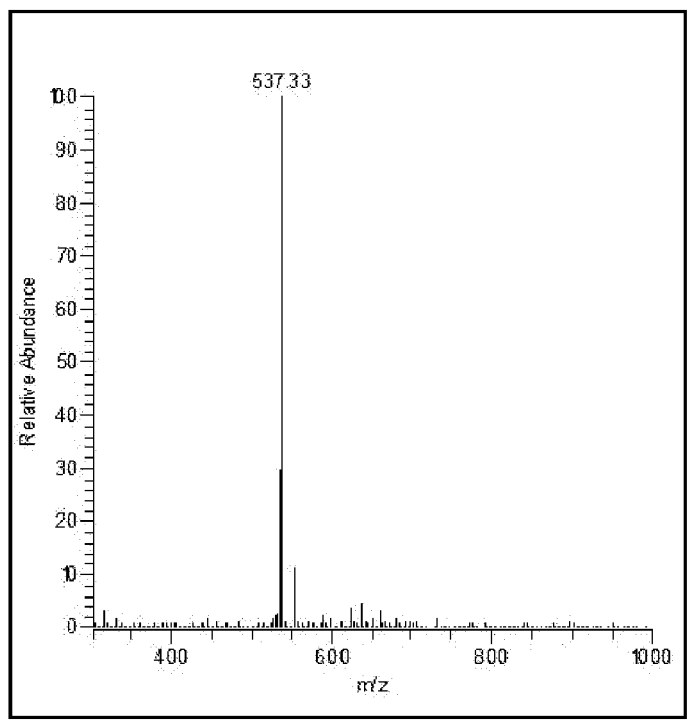

The following description illustrates embodiments of the invention. The following description is not to be construed as limiting, it is being understood that a skilled person in the art may carry out many obvious variations to the invention.

According to a particular embodiment of the present invention, the process of preparing guava pulp having high lycopene concentration comprises the steps of:

(a) Obtaining by-products of guava that are derived during crushing, refining and sieving steps in guava puree production processing line. The by-products are known as refiner, siever and decanter, respectively. The composition of decanter by-product does not contain any seeds or peels. This is the result of the last stage in the process for preparing the guava puree which is the starting material for the process of the present invention. This by-product has a moisture content of approximately 80%. The lycopene content of this by-product is 170 mg/kg dry matter, as determined by high performance liquid chromatography.

(b) Steam blanching the by-product for thermal stabilization of components in the by-product using steam blanching at a temperature ranging from 50° C. to 65° C. under a condition that permits evaporation of vapors inside the container for 20-60 minutes. Steam blanching significantly increased the lycopene content by 13% compared to the non-blanched by-product.

(c) Slicing the steam blanched guava by-product to obtain a thin layer sheet of about 1 to 3 mm thickness. The thin layer sheet was transferred to a tray for drying process. Then, the tray is subjected to drying at 40° C. to 60° C. for 5 to 7 hours. Drying of the thin layer sheet removes about 50% of the water contained in the by-products.

(d) Grinding the dried by-product and passing through the sieve to obtain consistent particle size of not greater than 0.25 mm.

After completion of the above steps, a guava pulp composition in the form powder is obtained, wherein the particle size is not greater than 0.25 mm and preferably having a moisture content of less than 30%. The powder has high antioxidant capacity and can be used as a substrate for extraction of antioxidant component. The resulting powder has the following advantages:
  i. Inexpensive source of starting material for obtaining guava oleoresin and lycopene.
  ii. A safe food ingredient from natural sources which may also have health benefits.
  iii. Minimize the disposal of this by-product which presents a major problem by industry.

According to a further embodiment of the present invention, the pulp obtained by the present process (hereinafter also referred to as pulp composition), wherein the particle size is not greater than 0.25 mm and the lycopene concentration in the pulp is 1 to 2 folds higher than in the guavas from which the composition is obtained. The composition further does not contain any seeds or peels. This is a result of decanting process carried out at the final stage of processing line. This step effectively removes seeds, peels and other particles, however, some pieces of peels or seeds may remain in a negligible amount for all practical purposes. The relatively small particle size of the pulp of the present invention allows for easier drying. The drying of the pulp removes about 50% water contained in the in the guavas from which the pulp is obtained.

In a yet further embodiment of the present invention, guava oleoresin and lycopene may be obtained from the pulp composition of the present invention. Hence, the present invention provides the use of the pulp composition as starting material for obtaining guava oleoresin and lycopene.

According to a further embodiment of the present invention, the composition described herein may be used as an antioxidant due to its ability to inhibit lipid oxidation.

The present invention will now be described in further detail by way of examples.

EXAMPLES

Example 1

Preparation of Guava By-Products/Wastes

Guava fruits used in the present invention are derived from pink guava tree, which is scientifically known as *Psidium guajava*. By-products or wastes of the guava fruit, such as refiner, siever and decanter, are obtained from crushing, refining and sieving of the puree processing line with particle size less than 1.2 mm being put in a container. The guava pulp has a total solid concentration of approximately 88% moisture content.

Example 2

Process for Obtaining Guava Pulp

Approximately 30 g of the guava by-products or industrial waste was steam blanched at 50° C. to 90° C. under a condition that permits evaporation of vapors inside the container for 20 to 60 minutes. The resultant heat-treated sample was sliced to about 5×5 cm with sixteen 0.5 cm holes and 1 to 3 mm thickness to increase its surface area.

Next, the thin layer sheet was transferred onto a tray and subjected to drying at 40° C. to 60° C. for 5 to 7 hours. The dried samples were ground and passed through a sieve to obtain a consistent particle size of not more than 0.25 mm.

Example 3

Extraction of Lycopene

Lycopene content in the processed guava pulp was extracted using the method of Fish et. al. (2002) with some modifications. Guava pulp obtained from Example 2 was weighed in a test tube. A mixture of acetone containing synthetic antioxidant, 95% ethanol and hexane was added into the test tube and vortexed. Then, the test tube was shaked by an orbital shaker for a few minutes. After that, deionised water was added and the tube was shaked again. Finally, the mixture was allowed to undergo phase separation.

Example 4

Determination of Lycopene (a) Method 1: UV-vis Spectrophotometer

Hexane layer from the product in Example 3 was read in 1 cm path length quartz cuvette using UV-vis spectrophotometer at 503 nm with hexane as the blank. Lycopene content was estimated as mg/100 g dry basis of pink guava by-products based on the following equation:

$$\text{Lycopene (mg/100 g)} = \frac{A_{503}}{17.2 \times 10^4 M^{-1} \times cm} \times \frac{536.9 \text{ g}}{mol} \times \frac{10^3 \text{ mg}}{1 \text{ g}} \times \frac{10 \text{ ml}}{\text{kg sample}} \times \frac{1 \text{ l}}{10^3 \text{ ml}} = \frac{A_{503} \times 0.0312}{\text{kg sample}} = \frac{A_{503} \times 0.312}{100 \text{ g sample}}$$

where,
$A_{503}$=Absorbance of the sample extract at 503 nmMolar extinction coefficient for lycopene in hexane is $17.2 \times 10^4 M^{-1} \times cm$ (Zechmeister, Lerosen, Schroeder, Polgar, & Pauling, 1943)

Based on the dry weight basis, the lycopene content was in the range of 71 to 116 mg per kg. For wet basis, decanter was found to be highest in lycopene content compared to fruits, siever and refiner. The lycopene content based on wet basis was in the range of 13 to 23 mg per kg.

(b) Method 2: Reverse-Phase HPLC

The extraction of lycopene was followed according to method 1 with modifications. A sample from Example 3 was mixed with magnesium carbonate, then acetone containing BHT, 95% ethanol and hexane were added into conical flask. The mixture was shaked at 300 rpm using an orbital shaker. After about 20 minutes, the extract was filtered through a Whatman paper No. 4. The residual was re-extracted with the same volume of extraction medium for 20 minutes. Then, the extract was filtered and pooled, and the filtrate was added with deionized water and shaked at 200 rpm for 5 minutes. Finally, the mixture was allowed to separate for 5 minutes in a separating funnel. The upper part was passed through 1 g of anhydrous sodium sulphate. Then, hexane was evaporated using a rotary evaporator at 35° C. Appropriate volume of dichloromethane was used to dilute the resultant extract, and then filtered through 0.22 μm membrane filter and injected into HPLC system.

Chromatographic Conditions: The HPLC (Agilent 1100, Palo Alto, USA) was equipped with degasser, quaternary pump, autosampler and diode array detector was used. A reverse phase $C_{18}$ octadecyl silane ODS (5 μm particle size, 250 mm length×4.6 mm I.D) was used. The mobile phase and HPLC system conditions used were according to Wilberg and Rodriguez-Amaya with modifications. In this study, isocratic mobile phase was a mixture of acetonitrile: chloroform (92:8) with 0.1% of triethylamine (TEA). The column temperature was set at 21° C. and flow rate at 1.0 mL min$^{-1}$. Injection volume was 20 μL and the wavelength was set at 470 nm. The lycopene content was quantified using different standards at concentrations between 12.5-200 μg mL$^{-1}$.

Lycopene content of guava fruits and by-products on a wet basis and dry basis is provided in Table 1 and Table 2, respectively.

TABLE 1

Lycopene content of pink guava fruits
and by-products (mg/kg wet basis)

| | Wet Basis | | |
|---|---|---|---|
| Sample | all-trans-lycopene | cis-lycopene | Total lycopene |
| Fruits | 28.76 ± 0.53 | 9.01 ± 1.26 | 37.77 ± 1.58 |
| Refiner | 18.24 ± 0.38 | 10.39 ± 0.47 | 28.63 ± 0.09 |
| Siever | 21.28 ± 0.84 | 12.21 ± 0.62 | 33.49 ± 1.38 |
| Decanter | 36.47 ± 1.52 | 18.64 ± 2.34 | 55.11 ± 0.82 |

TABLE 2

Lycopene content of pink guava fruits
and by-products (mg/kg dry basis)

| | Dry Basis | | |
|---|---|---|---|
| Sample | all-trans-lycopene | cis-lycopene | Total lycopene |
| Fruits | 211.87 ± 3.87 | 66.41 ± 9.32 | 278.28 ± 11.65 |
| Refiner | 55.7 ± 0.12 | 31.73 ± 1.43 | 87.43 ± 0.27 |
| Siever | 79.69 ± 3.15 | 45.73 ± 2.33 | 125.42 ± 5.15 |
| Decanter | 112.99 ± 4.70 | 57.74 ± 7.25 | 170.73 ± 2.55 |

Example 5

Identification of Lycopene Isomers

The presence of lycopene in the sample obtained in Example 2 was identified by confirmation analysis using LC-MS (Finnigan LCQ Deca, San Jose, USA).

Chromatographic condition: The column of $C_{18}$ XDB extra dense bonding (5 µm particle sizes, 250 mm length×4.6 mm I.D) was used. The isocratic program with a mobile phase consists of acetonitrile:chloroform (92:8) with 0.1% of triethylamine (TEA) was used at a flow rate of 0.8 mL min$^{-1}$. The system was equipped with a computer software Finnigan X caliber. The conditions of the system were based on Mercadante et al.[4]. Positive mode atmospheric pressure chemical ionization (APCI) was applied. The capillary temperature was set at 120° C. and APCI vaporizer temperature was 400° C. Mass to charge ratio (m/z) was measured with full scan mass in the range of m/z 300-1000. Molecular weight of lycopene from sample was compared with the lycopene standard monitored at m/z 537. All-trans and cis-isomers were detected with all-trans-isomer to be higher than cis-isomer. Lycopene occurs naturally in all-trans-isomer and seven double bonds of its chain and can be isomerized to mono-cis or poly-cis due to exposure to high temperature, light, oxygen, acid, catalyst and metal ion. In this study, all the experimental procedures were carried out under subdued light. In order to confirm that both peaks of HPLC chromatogram belonged to lycopene isomers, LC-APCI-MS was used to determine the molecular weight of the compound in both peaks.

Figure 1B:
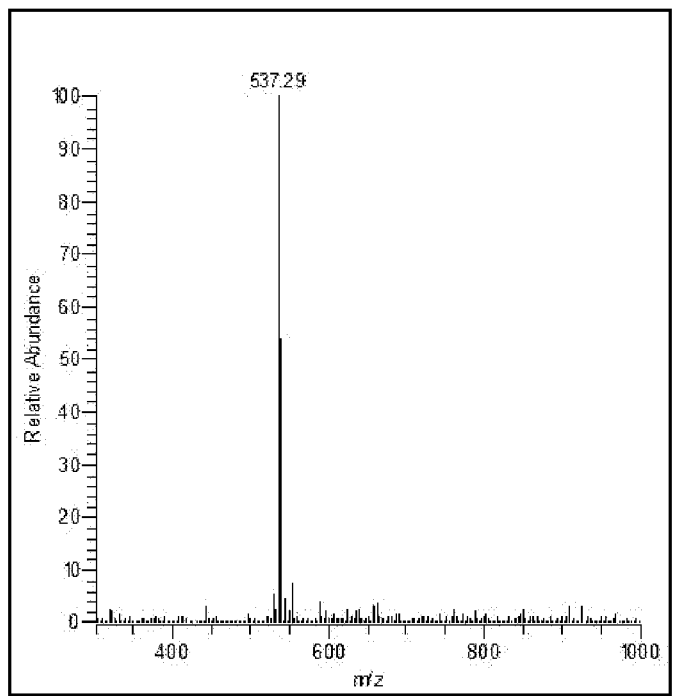

The results showed that lycopene was positively ionized. Protonated molecular ionization [M+H]$^+$ of the sample and lycopene standard are showed in FIGS. 1(a) and 1(b). Identification was done based on the retention time of the standard lycopene and the compound was confirmed based on the molecular lycopene ion. Mass spectrum showed both peaks have the same molecular ion at m/z 537. Therefore, the molecular weight of lycopene isomers was 537.

Example 6

Guava Pulp Composition as Antioxidant

Figure 2:
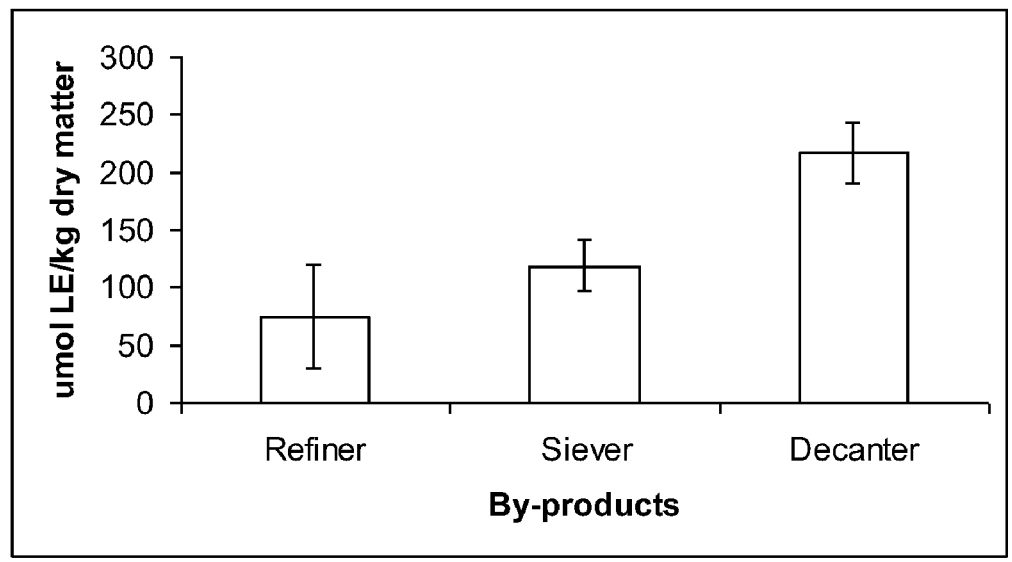
FIG. 2 shows an antioxidant capacity of a guava pulp composition according to the present invention.

Antioxidant capacity of pink guava industrial waste extract was determined based on the ability of the extract scavenged the stable 2, 2'-azinobis (3-ethylbenzothiazoline-6-sulfonic acid) radical cation (ABTS$^+$). The results were calculated based on the calibration curve plotted using lycopene at different concentrations (1.25-20 µg/ml). Results were expressed as µmol lycopene equivalents per kg of sample. This method is generally described by Re et al., Free Radical Biology and Medicine 26, 1999, 1231-1237. Referring to FIG. 2, the antioxidant capacity of the extract is more than 217 µmol lycopene equivalents/kg dry basis.

Example 7

Guava Pulp Composition as Agent for Inhibiting Lipid Oxidation

Figure 3:
FIG. 3 shows an antioxidant activity of a guava pulp composition according to the present invention based on inhibition towards lipid oxidation.

Inhibition of lipid oxidation was determined based on β-carotene bleaching assay. In this assay, linoleic acid produces hydroperoxides as free radicals during incubation at 50° C. The presence of antioxidants in the said extract will minimise the oxidation of β-carotene by hydroperoxides. Hydroperoxides formed in this system will be neutralized by the antioxidants from the extracts. Thus, the degradation rate of β-carotene depends on the antioxidant activity in the extracts. Results were expressed as percentage of antioxidant activity calculated based on the degradation rate of β-carotene. This method is generally described by Velioglu et al., J Agric Food Chem 46, 1998, 4113-4117. Referring to FIG. 3, the antioxidant activity of the extract in inhibiting lipid oxidation is more than 70%.

The invention claimed is:

1. A *psidium guajava* pulp composition wherein the composition has a particle size of not greater than 0.25 mm which does not contain seeds and peels from the *psidium guajava*, has a moisture content of less than 30% and has a lycopene concentration which is 1 to 2 folds higher than the lycopene concentration in the *psidium guajava* in the raw/unextracted state wherein said composition is made by crushing, refining and sieving the *psidium guajava* fruit to yield a *psidium guajava* pulp with a particle size less than 1.2 mm, the *psidium guajava* pulp is then stem blanched at 50° C. to 90° C. for 20-60 minutes in a container to evaporate the vapors inside the container to yield a resulting pulp, the resulting pulp is then sliced to about 5×5 cm with sixteen 0.5 cm holes and 1-3 mm thickness to increase the resulting pulp's surface area to form a thin layer sheet, then the thin layer sheet is subjected to drying at 40° C. to 60° C. for 5-7 hours to yield dried samples, the dried samples were then ground and passed through a sieve to obtain the *psidium guajava* pulp composition.

* * * * *